(12) United States Patent
Fathi Najafabadi

(10) Patent No.: US 10,196,555 B2
(45) Date of Patent: Feb. 5, 2019

(54) SUBTERRANEAN PRODUCING ZONE TREATMENT

(71) Applicant: Chevron U.S.A. Inc., San Ramon, CA (US)

(72) Inventor: Nariman Fathi Najafabadi, Sugar Land, TX (US)

(73) Assignee: CHEVRON U.S.A. INC., San Ramon, CA (US)

(*) Notice: Subject to any disclaimer, the term of this patent is extended or adjusted under 35 U.S.C. 154(b) by 513 days.

(21) Appl. No.: 14/885,735

(22) Filed: Oct. 16, 2015

(65) Prior Publication Data

US 2016/0024372 A1  Jan. 28, 2016

Related U.S. Application Data

(60) Provisional application No. 62/072,713, filed on Oct. 30, 2014.

(51) Int. Cl.
| | |
|---|---|
| *C09K 8/58* | (2006.01) |
| *E21B 49/08* | (2006.01) |
| *C09K 8/66* | (2006.01) |
| *G06F 19/00* | (2018.01) |
| *E21B 43/26* | (2006.01) |

(52) U.S. Cl.
CPC ............... *C09K 8/58* (2013.01); *C09K 8/66* (2013.01); *E21B 43/26* (2013.01); *E21B 49/087* (2013.01); *G06F 19/704* (2013.01)

(58) Field of Classification Search
CPC .. C09K 8/58; C09K 8/66; E21B 43/26; E21B 49/087
See application file for complete search history.

(56) References Cited

U.S. PATENT DOCUMENTS

| | | | | |
|---|---|---|---|---|
| 5,042,580 A | * | 8/1991 | Cullick | C09K 8/60 166/252.1 |
| 6,439,308 B1 | * | 8/2002 | Wang | C09K 8/58 166/270 |
| 8,573,299 B2 | * | 11/2013 | Dwarakanath | C09K 8/58 166/270.1 |
| 9,469,804 B2 | * | 10/2016 | Hernandez Altamirano | C09K 8/594 |
| 9,879,515 B2 | * | 1/2018 | Green | C09K 8/805 |
| 2003/0031788 A1 | * | 2/2003 | Espin | C09K 8/845 427/230 |
| 2012/0097389 A1 | * | 4/2012 | Dwarakanath | C09K 8/58 166/270.1 |

(Continued)

OTHER PUBLICATIONS

Ma, Morrow, Zhang, and Zhou. "Characterization of Wettability from Spontaneous Imbibition Measurements." Journal of Canadian Petroleum Technology. vol. 38, No. 1394 (1999): Paper: 94-47 (Year: 1999).*

*Primary Examiner* — Zakiya W Bates
*Assistant Examiner* — Crystal J Miller
(74) *Attorney, Agent, or Firm* — Karen R. DiDomenicis

(57) ABSTRACT

A preconditioning fluid is provided for producing crude oil from a subterranean formation. The preconditioning fluid produces an interface with crude oil in the formation that is more elastic than the interface between formation brine and the crude oil and has a favorable Amott-Harvey wettability index for oil recovery under the dominant hydrocarbon recovery mechanisms. The more elastic interface and improved Amott-Harvey wettability index is consistent with higher recoveries of crude oil from the formation.

19 Claims, 2 Drawing Sheets

(56) References Cited

U.S. PATENT DOCUMENTS

| | | | |
|---|---|---|---|
| 2012/0261120 A1* | 10/2012 | Del Gaudio | E21B 43/16 166/270.1 |
| 2013/0081812 A1* | 4/2013 | Green | E21B 43/267 166/280.1 |
| 2014/0151041 A1* | 6/2014 | Hernandez Altamirano | C09K 8/594 166/271 |
| 2016/0003018 A1* | 1/2016 | Saboowala | C09K 8/035 166/298 |

* cited by examiner

SUBTERRANEAN PRODUCING ZONE TREATMENT

CROSS-REFERENCE TO RELATED APPLICATIONS

The present application claims priority to U.S. Provisional Application Ser. No. 62/072,713, filed on Oct. 30, 2014, which is incorporated herein by reference in its entirety.

FIELD OF THE INVENTION

The present invention is directed to a process, a composition and a system for producing hydrocarbons from a hydrocarbon-bearing subterranean formation. In particular, the invention is directed to an aqueous fluid for preconditioning a hydrocarbon-containing formation during an enhanced oil recovery operation.

BACKGROUND OF THE INVENTION

Only a portion of the oil present in an oil-bearing subterranean formation is recoverable as a result of the natural pressure of the formation. The oil recovered from this "primary" recovery typically ranges from 5% to 35% of the oil in the formation. The oil that remains is trapped by capillary forces in the pore space of the oil-bearing formation, or is attracted to the formation through electrostatic or Vander Waals attraction, and will not easily flow to a production well.

It is well known that hydrocarbon bearing subterranean formations may be stimulated to initiate or to increase the production of hydrocarbon liquids and gases from the formation. Some of the methods for stimulation involve injecting water or an aqueous solution into the formation to facilitate hydrocarbon flow into a production well, through which the hydrocarbons are "produced" to the surface for processing and use. Secondary recovery methods include injecting fluids into the formation to increase formation pressure, and to displace hydrocarbons from the formation to production facilities. Waterflood fluids introduce an immiscible phase into the formation to drive oil in the formation to production wells. Gases such as natural gas, air and carbon dioxide which may be injected into the formation for secondary recovery decrease the density of the oil in the reservoir to improve oil flow through the formation and through the production well.

Enhanced, or tertiary oil recovery methods increase the mobility of the oil in order to increase extraction. Thermal methods may be employed to increase the formation temperature and decrease the oil viscosity. Thermal methods may also create or enhance porosity in the formation to facilitate the flow of oil to a production well. Steam injection and fire flooding are two thermal methods that have been successfully employed to increase oil production from heavy oil reserves. Using water containing a surfactant and optionally one or more polymers as a liquid flood may also be used. The surfactant is believed to reduce the surface tension between the water and the oil in the reservoir. Using water as a viscous drive to displace oil in the formation is substantially improved as an enhanced oil recovery method by the reduced surface tension between water and oil in the formation.

But conventional enhanced oil recovery methods fail to recover all of the available oil in many hydrocarbon bearing formations. One approach has been to modify a waterflood fluid in order to effect changes in the wettability of the inorganic matrix/crude oil interface in the pore spaces of the formation. Many different variations on this approach have been disclosed, with they appear to be limited to specific reservoirs. The principles cannot be applied generally across the oil production space.

Additional recovery tools are needed for recovering the residual oil remaining in capillaries and small cavities in the inorganic matrix of the formation. To dislodge this residual oil, an aqueous displacement fluid must include chemical properties for changing the wettability of the inorganic matrix in contact with oil and brine, or the clay that naturally resides on the inorganic matrix surface, and between the oil adsorbed to the surface and the surface itself. Much recent work has been directed to methods for effectively modifying the wettability of the inorganic matrix to increase oil production.

U.S. Pat. No. 5,148,705 describes a method and formation test tools for making in situ measurements in a borehole to determine wettability of a formation, particularly in zones of irreducible water saturation. Wettability estimation can also be accomplished using the rock surface composition obtained by XPS (x-ray photoelectron scattering), and correlating it with the amount of organic carbon absorbed on the surface. Accordingly, the entire disclosure of U.S. Pat. No. 5,148,705 is incorporated herein by reference.

But the process of extracting the trapped oil from cavities and capillaries in the formation involves several mechanisms, including reducing the oil/rock attraction in the capillaries and then displacing the oil droplets from the cavities without breaking the droplets in such a way that only a fraction of the oil in the capillaries is removed and recovered. Most recently published methods for recovering oil have focused on the ionic profile of the waterflood fluid (e.g. US20140041856, U.S. Pat. No. 7,987,907 and US20120143579). These methods have not fully addressed the multiple processes involved in removing the remaining oil from the oil-bearing formation. Additional developments are necessary to improve the effectiveness of tertiary oil recovery methods.

SUMMARY OF THE INVENTION

In one embodiment, the invention relates to a method for enhancing the production of crude oil from a subterranean formation that contains crude oil and formation brine, comprising: preconditioning the subterranean formation with a preconditioning fluid comprising: a base fluid; and an interface elasticity agent in an amount: such that the interface elasticity of the preconditioning fluid and the crude oil is at least 10% greater than the interface elasticity of the formation brine and the crude oil; and such that the interfacial tension of the preconditioning fluid with the crude oil is within a factor of 3 of the interfacial tension of the formation brine with the crude oil; the preconditioning fluid having an ionic strength such that the subterranean formation in contact with the preconditioning fluid has an Amott-Harvey wettability index in a range from 0 to 1.0; and injecting a aqueous displacement fluid into the formation, the aqueous displacement fluid having an ionic strength within a factor of 1.5 of the ionic strength of the preconditioning fluid. In one embodiment, the aqueous displacement fluid contains in a range from 0 to 5000 mg/l of a polymer; in one embodiment, from 100 to 5000 mg/l of a polymer.

In one embodiment, the invention relates to a method for preparing a preconditioning fluid for enhanced crude oil production from a subterranean formation, comprising: collecting a production brine, a crude oil and a formation rock sample from the subterranean formation and determining the interfacial tension of the production brine in contact with the crude oil and the elasticity of the crude oil and the production brine, and further determining the Amott-Harvey wettability index of the production brine in contact with the formation matrix sample; forming a preconditioning fluid containing salt and having an ionic strength such that the formation matrix sample in contact with the preconditioning fluid has an Amott-Harvey wettability index in a range from 0 to 1; and blending a sufficient amount of an interface elasticity agent with the preconditioning fluid, such that: the interface elasticity of the preconditioning fluid and the crude oil is at least 10% greater than the interface elasticity between the production brine and the crude oil; and the interfacial tension between the preconditioning fluid and the crude oil is within a factor of 3 of the interfacial tension between the formation brine and the crude oil.

In one embodiment, the invention relates to a computer-implemented method for determining physical and chemical properties of a preconditioning fluid and a displacing fluid. The computer implemented method includes receiving measurement data associated with one or more characteristics of a rock formation sample, a crude oil sample, and a formation brine sample of a subterranean formation. The computer implemented method includes using said measurement data in a predictive model to determine physical and chemical properties of a preconditioning fluid and a displacing fluid for enhancing production of that crude oil from that rock formation. The predictive model sets the physical and chemical properties of the preconditioning fluid such that an interface elasticity of the preconditioning fluid and the crude oil in the rock formation is at least 10% higher than an interface elasticity of the formation brine and the crude oil in the rock formation. The computer implemented method includes outputting the determined physical and the chemical properties of the preconditioning fluid and the displacing fluid. The preconditioning fluid and the displacing fluid with those determined physical and chemical properties can be injected into a wellbore for producing that crude oil from that rock formation.

BRIEF DESCRIPTION OF THE DRAWINGS

These and other features of the present disclosure will become better understood with regard to the following description, claims and accompanying drawings where:

DETAILED DESCRIPTION OF THE INVENTION

Definitions

Figure 1:
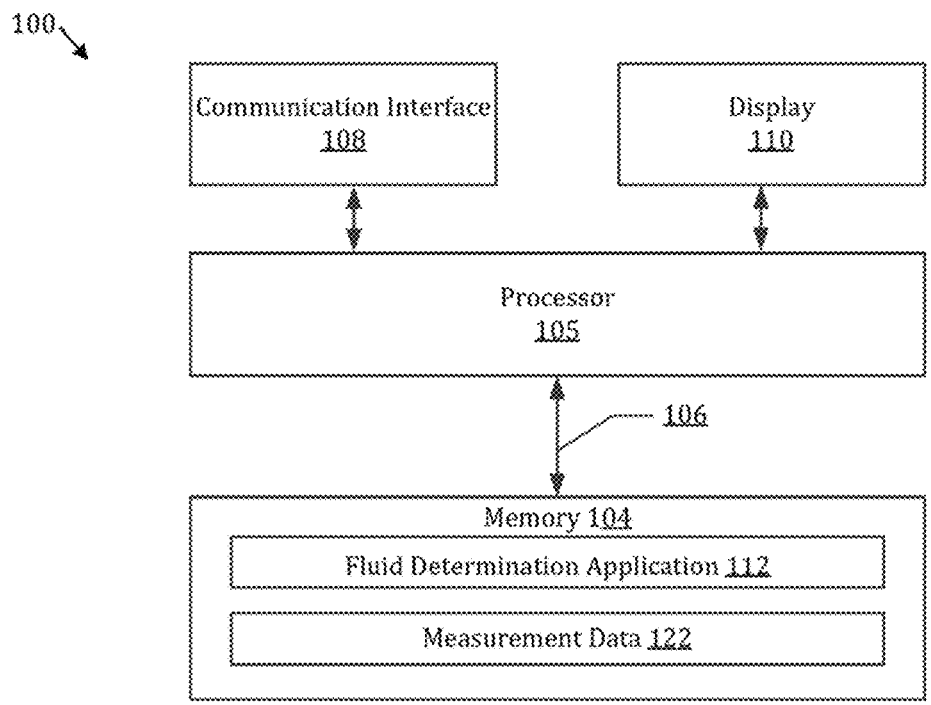
FIG. 1 illustrates a computing system useable for determining physical and chemical properties of a preconditioning fluid and a displacing fluid.

For purposes of this application, the term "formation" or "subterranean formation" refers to a subterranean geological structure. The term "hydrocarbon-containing formation" refers to a geological structure in which is disposed at least one of solid, liquid and gaseous hydrocarbons. Unless otherwise indicated, the terms "formation" and "hydrocarbon-containing formation" are used interchangeably to indicate the hydrocarbon containing portion of a subterranean formation.

For purposes of this application, the term "fracturing fluid" or "hydraulic fracturing fluid" is intended to mean fluid that is injected into a subsurface formation for performing hydraulic fracturing of the formation, as is typically understood by those skilled in the art. While fracturing fluid is generally composed primarily of water, fracturing fluid also includes various additives that affect the ability of the fracturing fluid to perform its intended function. Non-limiting examples of such additives include friction reducers, scale inhibitors, biocides, and dispersants, such as iron dispersants.

For purposes of this application, the term "formation brine" refers to water that occurs naturally within the pores of the inorganic matrix of the subterranean formation. The term "connate brine" refers to water that is trapped in the pores of a rock during its formation. "Connate brine" may be otherwise termed "fossil brine".

The base material is the subterranean formation that contains crude oil and formation brine is an inorganic matrix of rock in which the crude oil and brine are bound. A clay layer distinct from the bulk inorganic matrix of the formation may reside in the interface between the inorganic matrix and the fluids.

For purposes of this application, the term "production fluid" is intended to indicate fluid that is recovered as part of a subsurface oil or gas extraction operation. The term may refer to gases, liquids, or a combination. The term may refer to aqueous or hydrocarbon fluids or a combination. The terms "production water" and "production brine" are intended to indicate the aqueous production fluids from the extraction operation. Production brine is typically characterized as being a highly ionic, and thereby a conductive, aqueous solution.

For purposes of this application, the terms "hydrocarbon" or "hydrocarbonaceous" or "petroleum" are used interchangeably to refer to carbonaceous material originating from subterranean sources, including organic liquids or gases, kerogen, bitumen, crude oil, natural gas or from biological processes, that is principally hydrogen and carbon, with significantly smaller amounts (if any) of heteroatoms such as nitrogen, oxygen and sulfur, and, in some cases, also containing small amounts of metals. Crude oil (i.e. liquid petroleum) and natural gas (i.e. gaseous petroleum) are both hydrocarbons.

For purposes of this application, the term "produced hydrocarbons" is intended to mean the hydrocarbons that are recovered from a hydrocarbon-bearing subterranean formation. Unless otherwise specified, "produced hydrocarbons" refers to the particular hydrocarbons that are present in the formation, whether liquid, or gaseous, or both.

For purposes of this application, the term "natural gas" refers to a multi-component gas obtained from a crude oil well (associated gas) or from a subterranean gas-bearing formation (non-associated gas). The composition and pressure of natural gas can vary significantly. A typical natural gas stream contains methane (C1) as a significant component. Raw natural gas will also typically contain ethane (C2), higher molecular weight hydrocarbons, one or more acid gases (such as carbon dioxide, hydrogen sulfide, carbonyl sulfide, carbon disulfide, and mercaptans), and minor amounts of contaminants such as water, nitrogen, iron sulfide, wax, and crude oil.

For purposes of this application, the term "waterflooding" refers to a method of hydrocarbon recovery in which water is injected into a subterranean formation to displace oil and physically sweep the displaced oil to adjacent production wells. Displacement may involve bulk displacement of crude oil from the formation to a production well, as well as imbibition displacement from pores and other small liquid-containing capillaries.

For purposes of this application, the term "fracturing" refers to a method for increasing the accessibility of a hydrocarbon-bearing formation to fluid flow, using a fluid at a high pressure to create and enhance fractures in the formation. A fracturing fluid used in "hydraulic fracturing" is a water based fluid, optionally containing one or more additives.

For purposes of this application, the term "injection well" is intended to mean a wellbore extending into a subterranean formation for supplying a fluid to the formation to enhance hydrocarbon production from the formation. The fluid may be an aqueous or hydrocarbon-based fluid, which is injected through the injection well for dislodging hydrocarbons from the formation, for displacing and producing hydrocarbons, and, in some cases, for increasing the permeability of the formation to fluid flow through the formation. For purposes of this application, the term "production well" is intended to mean a wellbore extending into a subterranean formation for recovering production fluids from the formation. In one embodiment, one or more wellbores in the formation are operated first as an injection well for injecting a fluid into the formation, and subsequently operated as a production well for recovering fluids from the formation. In one embodiment, one or more wellbores in the formation are operated as an injection well, and one or more wellbores are operated as a production well.

For purposes of this application, the term "salt" refers to a composition of at least one cation and at least one anion that forms ions in aqueous solution. The ions may include such cations as sodium, potassium, calcium, barium, magnesium, ammonium, tetraalkylammonium, and the like. The salts may also such anions as chloride, bromide, iodide, carbonate, bicarbonate, sulfate, bisulfate, borate, phosphate, nitrate, silicate, acetate and citrate, and the like.

For purposes of this application, "salt concentration" of a particular aqueous solution is a measure of the amount of one or more ions dissolved in the solution. Exemplary ions include sodium, potassium, calcium, magnesium, barium, ammonium, tetraalkylammonium, chloride, bromide, iodide, carbonate, bicarbonate, sulfate, bisulfate, borate, phosphate, nitrate, silicate, acetate and citrate. By "dissolved" is meant the property of being able to pass through a 0.2 µm filter.

For purposes of this application, the term "pore volume" refers to the swept volume between an injection well and a production well and may be readily determined by methods known to the person skilled in the art. Such methods include modeling studies. However, the pore volume may also be determined by passing a high salinity water, including a tracer, through the formation from the injection well to the production well. The swept volume is the volume swept by the displacement fluid averaged over all flow paths between the injection well and production well.

For purposes of this application, the term "pressure" is the force exerted per unit area by a fluid, including hydrocarbon, water or mixtures, on the walls of a volume. Pressure can be shown as pounds per square inch (psi). "Atmospheric pressure" refers to the local pressure of the air. "Absolute pressure" (psia) refers to the sum of the atmospheric pressure (14.7 psia at standard conditions) plus the gage pressure (psig). "Gauge pressure" (psig) refers to the pressure measured by a gauge, which indicates only the pressure exceeding the local atmospheric pressure (i.e., a gauge pressure of 0 psig corresponds to an absolute pressure of 14.7 psia). The term "vapor pressure" has the usual thermodynamic meaning. For a pure component in an enclosed system at a given pressure, the component vapor pressure is essentially equal to the total pressure in the system.

For purposes of this application, the terms "enhanced oil recovery" or "EOR" refer to processes for enhancing the recovery of hydrocarbons from subterranean reservoirs.

For purposes of this application, the terms "interfacial tension" or "IFT" refer to the surface tension between test oil and water of different salinities containing a surfactant formulation at different concentrations. Typically, interfacial tensions are measured using a spinning drop tensiometer or calculated from phase behavior experiments.

The process for enhancing the production of crude oil from a subterranean formation may either be a crude oil displacement process, in which a fluid added to the formation displaces crude oil from the formation to a production well, or a fracturing process in which a fluid is injected into a formation for increasing the accessibility of liquids in the formation to fluid flow. Displacement of crude oil to a production well may involve imbibition displacement from pores and other small liquid-containing capillaries.

In the process, fluids may be injected into the formation through one or more wells, and produced fluids may be recovered from the formation through one or more of the same, or different, wells. In one method of enhanced production of crude oil or natural gas from a subterranean, hydrocarbon-bearing formation or reservoir, a displacement fluid is injected into the reservoir through an injection well and production fluids recovered from a production well which is at a horizontal distance or offset from the injection well. In practice, more than one injection well and more than one production well may be used and these may be arranged in a number of different patterns suitable for operations of this kind. For example, the wells may be arranged in a line drive wherein injection wells are arranged in a line and the production wells in lines parallel to the injection wells or in a pattern such as a five spot, seven spot, inverted seven spot or other conventional patterns well recognized by those skilled in the art. For ease of description, the present invention is described below with reference only to a single injection well and a single production well.

The enhanced production of crude oil includes at least two stages: a preconditioning stage involves injecting an aqueous preconditioning fluid into the formation for mobilizing oil in pore spaces within the formation; a following displacement stage involves displacing oil from the formation to the production well using an aqueous displacement fluid. The invention is based, at least in part, on the discovery that physiochemical processes that mobilize the oil trapped in pores in the formation and the physiochemical processes that displace the oil to a production well requires fluids of differing properties. Conventional methods that are intended to combine mobility and displacement using a single fluid adds significant costs to the operation and leaves significant amounts of unrecovered oil in the formation. The preconditioning fluid is formulated to modify the wettability of a clay layer at the inorganic matrix/crude oil interface within the pore structure of the formation. It is further formulated to enhance the elasticity of the crude oil/water interface within the pore structure of the formation. In this way, the preconditioning fluid significantly increases the effectiveness of the following modified waterflood fluid that is formulated to enhance the displacement of mobilized oil from the formation for production and recovery.

As disclosed herein, a hydrocarbon-bearing formation is first preconditioned to mobilize crude oil that is trapped within the pores and capillaries of the formation; the mobilized oil is then displaced by a water drive to production facilities. In this way, a significantly greater fraction of oil trapped within the formation is liberated and mobilized, while the bulk of the fluid used to displace the liberated oil need not contain the specialty chemicals present in the preconditioning fluid for mobilizing the oil.

In its natural state, the inorganic matrix/oil interface within the pores and capillaries may be either water wet, neutrally balanced, or oil wet. Properties of the inorganic matrix, the oil, the clay layer at the interface (if present), and any brine that is present interacts at the interface to determine its wettability characteristics.

The oil trapped in the pores and capillaries is mobilized when the rock wettability ranges from slightly oil wet (Amott-Harvey wettability index=−0.5) to totally water wet (Amott-Harvey wettability index=1). In one embodiment, the subterranean formation in contact with the preconditioning fluid has an Amott-Harvey wettability index in a range from 0 to 1.0; in another embodiment, in a range from 0.1 to 1.0. The desired wettability condition depends on the recovery mechanism. In embodiments, the method is useful for either fractured or non-fractured formations. In conventional non-fractured reservoirs, or where the viscous displacement of oil by water is the dominant recovery mechanism, the corresponding Amott-Harvey wettability index of the interface is in a range from 0.0 to 0.5; or in a range from 0.1 to 0.3; for example having a value of 0.1 (i.e. weakly water-wet). In naturally fractured reservoirs or where spontaneous imbibition of injected water from the fracture system into the matrix and subsequent release of oil from the matrix into the fracture system is the dominant recovery mechanism (such as diatomite and naturally fractured carbonates), the formation is desirably strongly water wet, having a Amott-Harvey wettability index in a range from 0.1 to 1.0; or from 0.3 to 1.0; or from 0.5 to 1.0.

Fractured formations may be alternatively naturally fractured or fractured by an enhanced method, such as hydraulic fracturing or gas fracturing or thermal fracturing. Such fracturing methods are well known. In one embodiment, the fractured formation is naturally fractured.

The extent of reservoir fracturing is based on the flow capacity index (FCI), defined as:

$$FCI = \frac{(Kh)_{well}}{(Kh)_{matrix}},$$

where K denotes permeability and h denotes reservoir thickness, $(Kh)_{well}$ represents a measured permeability product from well testing or pressure transient analysis, and $(Kh)_{matrix}$ is an average value of a core sample from the producing zone of the formation. An FCI value of greater than 3 means that the well is exhibiting 3 times more flow capacity than would have been expected from the matrix permeability determination; the formation is therefore considered to be fractured and the fractures are contributing to the extra flow capacity. An FCI is a range from 1 to 3 is indicative of a non-fractured formation.

In the method, a preconditioning fluid is prepared with an Amott-Harvey wettability index in a range from 0.0 to 0.5, and in an embodiment in a range from 0.1 to 0.3, when the FCI of the formation has a value in a range from 1 to 3. Alternatively, a preconditioning fluid is prepared with an Amott-Harvey wettability index in a range from 0.3 to 1.0, and in an embodiment in a range from greater than 0.5 to 1.0, when the FCI of the formation has a value of greater than 3.

The wettability of the inorganic matrix/oil interface in the pores and capillaries may be predicted from a wettability determination of core samples from the formation, using, for example, the Amott Wettability Method. The Amott Wettability Index is a ratio of the saturation change of the core sample by spontaneous imbibition to the saturation change by both spontaneous imbibition and forced displacement. The Amott method combines both capillary and viscous force effects to measure the average wettability of the core samples. A core sample is prepared by centrifuging under oil until irreducible water saturation (Swirr), placed into a water-filled tube where water spontaneously imbibes over a period of time until attaining equilibrium. The time required for equilibrium of the spontaneous imbibition recovery is a function of rock and fluid properties and could require a significant length of time in certain circumstances such as low matrix permeability, high oil viscosity, etc. In embodiments, equilibration occurs over a period of time ranging generally from 10 day to 30 days, though the test may be extended for low matrix permeability or high oil viscosity conditions. The sample is placed in a flow cell for forced displacement of oil by water until reaching residual oil saturation (Sor). The process is then reversed for spontaneous and forced oil imbibition, driving the water out of the core sample until reaching irreducible water saturation (Swirr). Separate ratios of spontaneous imbibition to total saturation change for water, $I_w$, and oil, $I_o$, are termed the water and oil imbibition indices, respectively. Preferentially water-wet cores have a positive displacement-by-water ratio and a zero value for the displacement-by-oil ratio. The displacement by-water ratio approaches +1 as the water wetness increases. Similarly, oil-wet cores have a positive displacement-by-oil ratio and a zero displacement-by-water ratio. Both ratios are zero for neutrally wet cores. The Amott-Harvey index, $I_{AH}$, combines the two ratios ($I_w$ and $I_o$) into a single wettability index. It is defined as the difference between the water spontaneous imbibition ratio, $I_w$, and that of the oil, $I_o$, ($I_{AH}=I_w-I_o$). The result is a number between +1 (strongly water-wetting) and −1 (strongly oil-wetting). If the oil ratio ($I_o$) has positive value and the water ratio ($I_w$) is zero, then the core is preferentially oil wet. Contrary to this, when the water ratio ($I_w$) has positive value and the oil ratio ($I_o$) is zero, it means that the core sample is preferentially water wet. If both values are zero, then the core is neutrally wet. U.S. Pat. No. 8,768,628 discloses the Amott-Harvey wettability index in detail, and is incorporated herein by reference.

The preconditioning fluid is a saline solution having an ionic strength such that the inorganic matrix/crude oil interface has an Amott-Harvey wettability index in a range from 0 to 1.0. While there are a number of components that may be present in the preconditioning fluid to affect the Amott-Harvey wettability index, the index is generally increased up to a limiting value of 1.0 by addition/subtraction of salt to the preconditioning fluid. The target ionic strength of the preconditioning fluid is established by the type of formation being treated for increased oil production. In one embodiment, for non-fractured reservoirs, the target Amott-Harvey wettability index is in a range from 0.1 to 0.5; or in a range from 0.1 to 0.3; or has a value of about 0.1. In another embodiment, for naturally fractured reservoirs or where spontaneous imbibition of injected water from the fracture system into the matrix and subsequent release of oil from the matrix into the fracture system is the dominant recovery mechanism (such as diatomite and naturally fractured carbonates), the target Amott-Harvey wettability index is in a range from 0.1 to 1.0; or from 0.3 to 1.0; or from 0.5 to 1.0.

The preconditioning fluid has an ionic strength to meet the target Amott-Harvey wettability index for the particular type of formation. In general, the preconditioning fluid has an ionic strength in a range from 0.001M to 5M. In alternative embodiments, the ionic strength of the preconditioning fluid is in a range from 0.001M to 0.03M; or in a range from 0.03M to 0.2M; or in a range from 0.2M to 1M; or in a range from 1M to 5M.

Ionic strength, as used herein, is defined by the equation $$I = \tfrac{1}{2} \Sigma_{i=1}^{n} c_i z_i^2 \quad (1)$$

where I is the ionic strength, c is the molar concentration of ion i, z is the valency of ion i, and n is the number of ions in the measured solution.

The salt content of the preconditioning fluid in terms of TDS (total dissolved salt) content is in a range from 500 to 300,000 mg/l TDS. There are a number of separate ranges that are embodiments of the broad range of TDS, including a range from 500 to 2000 mg/l TDS; in a range from 1000 to 20,000 mg/l TDS; in a range from 10,000 to 50,000 mg/l TDS; or in a range from 50,000 to 300,000 mg/l TDS.

The preconditioning fluid contains monovalent cations such as $Na^+$, $K^+$, or combinations, and divalent cations such as $Mg^{2+}$, $Ca^{2+}$, $Sr^{2+}$, $Ba^{2+}$, or combinations. The molar concentration of monovalent cations in the preconditioning fluid is in a range from 0.001M to 5M. In alternative embodiments, the molar concentration of monovalent cations in the preconditioning fluid is in a range from 0.001M to 0.03M; or in a range from 0.01M to 0.4M; or in a range from 0.2M to 1M; or in a range from 1M to 5M. The molar concentration of divalent cations in the preconditioning fluid is in a range from 0.001M to 5M. In alternative embodiments, the molar concentration of divalent cations in the preconditioning fluid is in a range from 0.001M to 0.03M; or in a range from 0.03M to 0.2M; or in a range from 0.2M to 1M; or in a range from 1M to 5M. The molar ratio of monovalent cations to divalent cations in the preconditioning fluid is in a range from 100:1 to 1:100. In alternative embodiments, the molar ratio of monovalent cations to divalent cations in the preconditioning fluid is in a range from 50:1 to 1:5; or in a range from 10:1 to 1:2; or in a range from 5:1 to 1:1.

The anions that are present in the saline preconditioning fluid are generally selected from the halides (e.g. $Cl^-$, $Br^-$, and $I^-$), borates (e.g. borate and metaborate), silicate, nitrate, carbonate, citrate, acetate, sulfate, phosphate or any combination thereof. In alternative embodiments, the anions are selected from the group consisting of nitrate, sulphate, borate, metaborate and phosphate; or selected from the group consisting of $Cl^-$ and $Br^-$.

The base fluid on which the preconditioning fluid is based is primarily aqueous. The base fluid may include fresh water, wastewater, saline solution, or a combination. The fresh water may originate from, for example, a stream, a lake or other surface body of water, or from an underground aquifer or other source of fresh water. Wastewater may originate from municipal or industrial sources. Suitable saline solutions include seawater, produced water from the hydrocarbon-containing subterranean formation, or from one or more wells in saline or brackish aquifers in other subterranean formations including aquifers above and/or below the hydrocarbon-containing subterranean formation. In embodiments, the base fluid includes formation brine, which is native to the formation. In embodiments, the base fluid includes production water from the formation, some of which is derived from water provided to the formation during operations such as drilling, fracturing, stimulation and production.

The salt-containing solution may be derived from a formation brine, or it may be a mother solution, a highly concentrated salt solution that is prepared as a standard source fluid for the preconditioning fluid.

Production water may be processed prior to use in the preconditioning fluid. The processing may include, for example, separating an aqueous phase from an organic phase with which it is produced from the formation. Methods for separating hydrocarbons from water in the context of produced fluids are known. Two-phase separation, cyclone and hydrocyclone separation, centrifugation, settling, filtering, and activated flocculation and sedimentation are exemplary methods for separating produced water from hydrocarbons, and other liquids and solids that may be present in the produced fluids. Dissolved organic molecules may be removed, for example, by oxidation, by changing pH, by salting out the organic phase, or by other methods known to reduce the solubility of organic molecules in water. Flocculants may be added to aid precipitation of slightly soluble species in the aqueous fluid.

Salts may be added to the base fluid in solid form or in a mother solution to achieve the target production fluid ionic strength. When used to adjust the salt content of the base fluid, the mother solution is a highly concentrated salt solution that is prepared as a standard source fluid for the preconditioning fluid.

Core samples used for determining the composition of the preconditioning fluid for the preconditioning process may be recovered from the formation using conventional methods. The coring fluid used for freeing the core samples from the formation matrix is generally selected to minimize any physical or chemical effects that would potentially compromise the quality of the samples. The coring fluid may be a blend water-based fluid, containing, for example, XC-polymer (xanthan gum biopolymer), dextrid, and CMC (carboxymethyl cellulose) to control the rheology. Prior to analysis, the core samples may be isolated in brine from light and air. Experimental methods are well known for contacting a core sample with an experimental preconditioning fluid under conditions of varying pressure to identify concentrations that result in wettability indices in the desired range.

For the purpose of this application, the term "interface elasticity agent" or alternatively "interface elasticity modifying agent" refers to any chemical compound that can accumulate at the interface between the oil and water and increase its elastic modulus. The interface elasticity agent may be an alcohol such as alkylaryl alkoxy alcohols, alkyl alkoxy alcohols, or from the family of alkyl alkoxylated esters, and alkyl polyglycosides or a surfactant such as nonionic or anionic, or other surface active molecules.

The preconditioning fluid is formulated with an interface elasticity modifying agent to increase the elasticity of the interface between the fluid and the crude oil in the rock matrix relative to that of the crude oil/formation water interface. During preconditioning, while the preconditioning fluid is being imbibed into the pores and capillaries of the rock matrix, the interface elasticity modifying agent is adsorbed on the interface between the preconditioning fluid and the oil in the pores. This increases the elasticity of the interface enabling it to pass through tortuous paths in the pore system more efficiently and leaving less oil behind, which enhances oil production from the formation. Disconnection of the oil ganglia passing through constantly expanding and contracting porous paths (pore body to pore throat) results in division/separation of the oil ganglia due to rupture of the interface. The portion of the divided ganglia remaining behind the pore throat remains trapped and cannot be recovered given the balance of forces present in a waterflood. Increased elasticity of the interface between the oil and water decreases the saturation in which such rupture of the interface and division of ganglia occurs for any given pore throat size, thus increasing the amount of oil that can pass through any pore size and be recovered and decreasing the oil that is left behind in the subterranean formation.

In one embodiment, the interface elasticity agent is a non-ionic chemical. At very low concentrations in the preconditioning fluid, the non-ionic chemical increases the interface elasticity of the crude oil/preconditioning fluid interface without affecting the absorption characteristics of the capillary surfaces in which the crude oil occurs. Useful non-ionic chemicals may be selected from, for example, alkylaryl alkoxy alcohols, alkyl alkoxy alcohols, alkyl alkoxylated esters, and alkyl polyglycosides.

In an embodiment, the non-ionic chemicals are incorporated into the preconditioning fluid formulations to make them homogeneous solutions for easier and more effective field injection. The selection of the non-ionic chemical depends on the total acid number (TAN), total base number (TBN), crude-oil composition in the reservoir, and the compatibility with the make-up or injection brine. Standard phase-behavior tests must be conducted to screen for appropriate non-ionic chemicals. To reduce the number of candidate non-ionic chemicals for the phase-behavior screen, the following guidelines can be used.

The non-ionic chemicals should be soluble in the preconditioning fluid. Generally, this implies that the HLB (Hydrophillic-Lipophillic-Balance) for the non-ionic chemical must be fairly high, such as greater than 10 (HLB>10). The cloud point (CP) for the non-ionic chemical should also be above both surface temperatures, which typically range between 0 and 100° C., and reservoir temperatures, which typically range between 30 and 150° C. The cloud point is the temperature above which the non-ionic chemical becomes insoluble in the make-up or injection brine. In particular, it is the temperature at which the non-ionic chemical becomes hydrophobic enough to separate from the aqueous solution, thus becoming a colloidal suspension or macroemulsion. The hydrophobicity of non-ionic chemical generally increases with temperature. The non-ionic chemical may also be selected so that at a cooler surface temperature it imparts high water solubility and salt tolerance to the non-ionic solution.

Suitable non-ionic chemicals generally have the following characteristics. The lipophilic moiety (tail) is an alkyl chain with typically more than six (6) carbons, with or without an aromatic ring (phenyl) attached to it. This chain may be linear or branched. In some embodiments, $C_8$ to $C_9$ (or $C_8$-Φ to $C_9$-Φ) are effective alkyl chains for the non-ionic chemicals.

The hydrophilic moiety is an ethoxy (EO), propoxy (PO) or butoxy (BO) chain with more than two repeating units of EO, PO, or BO. In some embodiments, more than six (6) repeating units, such as EO, are present. In some embodiments, more than ten to twenty repeating units, such as EO, are present. Because the particular makeup of the preconditioning fluid is dependent on the characteristics of the subterranean formation and fluid therewithin, further testing of the solution is often performed using oil from the formation for which the solution will be injected into. In particular, additional phase-behavior tests using actual crude oil and injection brine at reservoir temperature are utilized for selecting the appropriate non-ionic chemical that will be used for enhanced oil recovery of a particular reservoir. Based on the results of these tests, the non-ionic chemical and other components of the solution can be optimized. Example non-ionic chemicals include alcohol alkoxylates such as alkylaryl alkoxy alcohols or alkyl alkoxy alcohols. Currently available alkoxylated alcohols include LUTENSOL® TDA 10EO and LUTENSOL® OP40, which are manufactured by BASF SE headquartered in Rhineland-Palatinate, Germany. NEODOL 25, which is manufactured by Shell Chemical Company, is also a currently available alkoxylated alcohol. Chevron Oronite Company LLC, a subsidiary of Chevron Corporation, also manufactures alkoxylated alcohols such as L24-12 and L14-12, which are twelve-mole ethoxylates of linear carbon chain alcohols. Other non-ionic chemicals can include alkyl alkoxylated esters and alkyl polyglycosides. In some embodiments, multiple non-ionic chemicals such as non-ionic alcohols or non-ionic esters or resins are combined. In some embodiments, a preconditioning fluid may include an interface elasticity agent, and the interface elasticity agent may be based on a silicone copolymer, a resin, a non-ionic surfactant, and combinations thereof. In one embodiment, the interface elasticity agent may be based on a silicone copolymer only. In one embodiment, the interface elasticity agent may be based on a resin only. In one embodiment, the interface elasticity agent may be based on a non-ionic surfactant only. In one embodiment, the interface elasticity agent may be based on a combination of a silicone copolymer and a non-ionic surfactant only. In one embodiment, the interface elasticity agent may be based on a combination of a silicone copolymer, a resin, and a non-ionic surfactant. In some embodiments, the preconditioning fluid may contain in a range from 0.01 to 1000 ppm of the interface elasticity agent. Other embodiments and examples are also within the scope of the disclosure. In some embodiments, the chemicals are non-halogenated or non-fluorinated. In some embodiments, the non-ionic chemical consists of molecules of carbon, hydrogen, and oxygen atoms. In some embodiments, the non-ionic chemical has a number average molecular weight of 500 with a range of preferred embodiments of 100 to 3000.

In one embodiment, the interface elasticity modifying agent is a silicone copolymer based on polyalkylene oxide modified poly(dimethylsiloxane) chains, such as poly(ethylene oxide)-poly(dimethylsiloxane)-poly(ethylene oxide) block copolymers.

The interface elasticity modifying agent is added to the preconditioning fluid in amounts such that the crude oil/preconditioning fluid interface elasticity is at least 10% greater than the crude oil/formation fluid interface elasticity. In one embodiment, the crude oil/preconditioning fluid interface elasticity is in a range from 1.1 to 5 times the crude oil/formation fluid interface elasticity; in one embodiment, in a range from 2 to 3 times the crude oil/formation fluid interface elasticity; in one embodiment, in a range from 5 to 100 times the crude oil/formation fluid interface elasticity. The interface elasticity agent is included in the preconditioning fluid in very small amounts, in order to increase the interface elasticity without significantly increasing the cost of the operations. In one embodiment, the preconditioning fluid contains in a range from 1 ppb to 1000 ppm of the interface elasticity agent; in one such embodiment, in a range from 10 ppb to 100 ppm of the interface elasticity agent.

For the purpose of this application, the term "interface elasticity" refers to the elastic modulus of a liquid-liquid interface. Interface elasticity is a measure of the amount of deformation (strain), for a given stress, the interface will sustain without rupturing. Interface elasticity has the units Pa m and can be measured using a double wall-ring apparatus according to C. F. Brooks, et. al., "An Interfacial Stress Rheometer to Study Rheological Transitions in Monolayers at the Air-Water Interface", *Langmuir* 1999, 15, 2450-2459.

The interface elasticity may be determined using at least one crude oil sample from the formation, in contact with an aqueous solution. In one embodiment, a base interface elasticity is determined for a crude oil/formation brine standard, with both the crude oil and the formation brine being recovered from the formation. This base interface elasticity is compared with that of the crude oil/preconditioning fluid system. In one embodiment, the interface elasticity of the preconditioning fluid and the crude oil is at least 10% greater than the interface elasticity of the formation brine and the crude oil.

A dynamic surface modulus (which is a complex number) can be defined as the proportionality factor relating the measured strain to the applied stress:

$$\sigma e^{i\omega t} = G^*(\omega)\gamma_0 e^{i(\omega t - \delta(\omega))}$$

where $G^*(\omega)$ is dynamic surface modulus, a is amplitude of the applied sinusoidal stress, $\omega$ is the frequency of the stress, and $\gamma_0$ is the amplitude of the strain resulting from the sinusoidal stress at the same frequency. The strain lags the stress by a phase angle $\delta(\omega)$. The equation above can be solved to directly provide the dynamic surface modulus:

$$G^*(\omega) = \frac{\sigma}{\gamma_0} e^{i\delta(\omega)} = G'(\omega) + iG''(\omega)$$

where $G'(\omega)$ is the surface storage or elastic modulus and $G''(\omega)$ is the surface loss or viscous modulus.

Phase angle $\delta(\omega)$ is a direct measure of the elastic or viscous character of the interface. When phase angle is 0°, the film is purely elastic and when it is 90° the film is purely viscous. So the goal of preconditioning fluid would be to minimize the phase angle. In the present preconditioning fluid, a low concentration of a non-ionic surfactant is added to the fluid; with the addition of the particular amount of surfactant, the phase angle is decreased, thereby increasing the elasticity of the interface to prevent separation/division of the oil ganglia and increase oil recovery.

In embodiments, the interface elasticity of the preconditioning fluid that contains an interface elasticity agent is greater than 10 Pa m; in embodiments, 0.0001 to 10 Pa m.

The interface elasticity agent is further selected with regard to changes in the crude oil/aqueous phase interfacial tension within the pores of the formation matrix. In particular, the type and amount of the interface elasticity modifying agent is selected such that the interfacial tension of the crude oil/preconditioning fluid system within the pores is changed by a minimal amount by addition of the preconditioning fluid. Thus, in one embodiment, the IFT of the crude oil/preconditioning fluid system is within a range from a fifth (⅕) to 1 (one) times the IFT of the crude oil/formation brine system. In one embodiment, the IFT of the crude oil/preconditioning fluid system is within a range of from a third (⅓) to a half (½) times the IFT of the crude oil/formation brine system. In one embodiment, the interfacial tension of the crude oil/preconditioning fluid is greater than 15 mN/m; in one embodiment, in a range from 15 to 45 mN/m; in one embodiment, in a range from 20 to 40 mN/m.

In one embodiment, the interfacial tension of the crude oil/preconditioning fluid is in a range from 10 to 45 mN/m.

"Interfacial tension" is a measurement of the surface energy present at an interface between two liquid phases that exhibit a phase boundary, such as an aqueous phase and a hydrocarbon phase. A high interfacial tension value (e.g., greater than about 10 dynes/cm) may indicate the inability of one fluid to mix with a second fluid to form a fluid emulsion. Interfacial tension may be measured at a known or fixed temperature and pressure using any number of techniques and systems know in the art, including, for example, spinning drop tensiometers, pendent drop techniques, and the like. Measurements using a pendent drop method may be conducted at the same pressure and temperature conditions, e.g., at reservoir conditions of about 30-90° C., or higher, and 1-4 atms, or higher.

The pH of the preconditioning fluid is selected for a particular formation. In alternative embodiments, the pH of the preconditioning fluid is in a range from 1-3; in a range from 3-6.5, in a range from 6 to 8; in a range from 7.5 to 9; or in a range from 9 to 13.

In the case of an acidic preconditioning fluid, the desired pH may be achieved by adding to the fluid, for example, one or more of an inorganic or an organic acid. Suitable examples include hydrochloric acid, hydrofluoric acid, sulfamic acid, formic acid, citric acid, boric acid, acetic acid, chlorinated acetic acid, carbon dioxide, gelled or emulsified acids, and mixtures thereof.

In the case of an alkaline preconditioning fluid, the desired pH may be achieved by adding to the fluid, for example, ammonia or an ammonium-containing solution, an organic amine, or a hydroxide such as NaOH or KOH.

In one embodiment, the method for preparing a preconditioning fluid for enhanced crude oil production from a subterranean formation includes collecting a production brine, a crude oil and a formation matrix sample from the subterranean formation and determining the interfacial tension of the production brine in contact with the crude oil and the elasticity of the crude oil/brine interface, and further determining the Amott-Harvey wettability index of the formation brine and crude oil in contact with the formation matrix sample; forming a preconditioning fluid containing salt and having an ionic strength such that the formation matrix sample in contact with crude oil and preconditioning fluid has an Amott-Harvey wettability index in a range from 0 to 1; and blending a sufficient amount of an interface elasticity agent with the preconditioning fluid, such that: the interface elasticity of the preconditioning fluid and the crude oil is at least 10% greater than the interface elasticity between the production brine and the crude oil; and the interfacial tension between the preconditioning fluid and the crude oil is within a factor of 3 of the interfacial tension between the formation brine and the crude oil. In some embodiments, a hydraulic fracturing fluid may include the preconditioning fluid, and the hydraulic fracturing fluid may be into a wellbore (e.g., a wellbore for hydraulic fracturing).

The preconditioning fluid may be prepared by blending the interface elasticity agent with the aqueous base fluid. A salt may be added to the aqueous base fluid prior to the blending step; alternatively, a salt may be added to the blend. In situations in which the aqueous base fluid contains excess of one or more salts, a portion of the salts may be removed from the base fluid, using known methods for salt removal. In some situations, one or more cations or anions may be removed to lower concentrations, while other of the cations or anions are retained for use in the preconditioning fluid. The concentration of salts in the base fluid may also be adjusted by the addition of fresh water, wastewater, saline solution, or a combination to achieve a target salt concentration in the preconditioning fluid. The salt concentration and the interface elasticity agent concentration in the preconditioning fluid may be adjusted in any order. In some situations, at least, the salt concentration in the preconditioning fluid is adjusted to a target level, following which the interface elasticity agent is added. Using this addition sequence reduces any deleterious effects that high salt concentrations may have on the interface elasticity agent.

The preconditioning fluid is injected into the hydrocarbon-containing formation prior to waterflooding the formation. In the case of a huff and puff process, a sufficient amount of the preconditioning fluid is injected into the formation to contact a region of the formation around the injection wellbore. For an injection wellbore(s)/production wellbore(s) system, a sufficient amount of the preconditioning fluid is injected into the formation to contact a region of the formation between injection and producing wellbores. In an embodiment, an amount of preconditioning fluid is injected into the formation equal to up to 2.0 pore volumes of the region of the formation selected for preconditioning. In an embodiment, an amount of preconditioning fluid is injected into the preselected region of the formation equal to in a range from 0.1 to 0.75 pore volumes of the formation; or equal to in a range from 0.1 to 0.5 pore volumes of the formation.

The preconditioning fluid may be injected at a pressure sufficient to cause the fluid to flow into the formation, up to or higher than the formation pressure. In a separate embodiment, the injection pressure is greater than the fracturing pressure of the formation, such that injecting the fluid creates and enhances fractures in the formation, so as to stimulate oil and/or gas production from the formation. The preconditioning fluid in the formation will be at the formation temperature, which may be greater than 130° F. (about 54° C.).

Prior to preconditioning, the hydrocarbon-bearing formation is in contact with formation brine that is characteristic of the formation or a blend of formation brine and previously injected brine, and the inorganic rock matrix of the formation may be characterized by a representative Amott-Harvey wettability index. As the preconditioning fluid is injected into the formation, the inorganic rock matrix begins to acquire an Amott-Harvey wettability index that is representative of the rock matrix/preconditioning fluid interaction, first near the injection wellbore, the region of preconditioning expanding from the injection wellbore(s) to the production wellbore(s) as time elapses and additional preconditioning fluid is injected. In one embodiment, sufficient preconditioning fluid is injected into the formation, such that a region of the hydrocarbon-bearing formation that encompasses at least one injection wellbore and at least one production wellbore in the formation achieves an Amott-Harvey wettability index in the target range. In one embodiment, for non-fractured reservoirs, the target Amott-Harvey wettability index is in a range from −0.3 to 0.5; or in a range from 0.0 to 0.3; or has a value of about 0.1. In one embodiment, for naturally fractured reservoirs or where spontaneous imbibition of injected water from the fracture system into the matrix and subsequent release of oil from the matrix into the fracture system is the dominant recovery mechanism (such as diatomite and naturally fractured carbonates), the target Amott-Harvey wettability index is in a range from 0.1 to 1.0; or from 0.3 to 1.0; or from 0.5 to 1.0.

As disclosed herein, preconditioning the formation involves contacting the formation with a preconditioning fluid comprising: an interface elasticity agent in an amount such that the interface elasticity between the preconditioning fluid and a hydrocarbon phase is at least 10% greater than the interface elasticity between the formation brine and the hydrocarbon phase; and such that the interfacial tension of the preconditioning fluid with the hydrocarbon phase is within a factor of 3 of the interfacial tension of the formation brine with the hydrocarbon phase; the preconditioning fluid having an ionic strength such that the subterranean formation in contact with the preconditioning fluid has an Amott-Harvey wettability index in a range from −0.3 to 1.

In another embodiment, preconditioning the formation involves contacting the formation with a first preconditioning fluid having an ionic strength such that the subterranean formation in contact with the preconditioning fluid has an Amott-Harvey wettability index in a range from 0 to 1. The formation is then contacted with a second preconditioning fluid that contains an interface elasticity agent in an amount such that the interface elasticity between the preconditioning fluid and a hydrocarbon phase is at least 10% greater than the interface elasticity between the formation brine and the hydrocarbon phase; and such that the interfacial tension of the preconditioning fluid with the hydrocarbon phase is within a factor of 3 of the interfacial tension of the formation brine with the hydrocarbon phase. In certain situations, the use of a smaller amount of the second preconditioning fluid, relative to the first preconditioning fluid, serves to decrease the cost of the interface elasticity agent, without affecting the recovery of hydrocarbons from the formation. In one embodiment, the volumetric ratio of the first preconditioning fluid to the second preconditioning fluid is in a range from 10:1 to 1:1. In alternative embodiments, the volumetric ratio is in a range from 5:1 to 1:1; or in a range from 2:1 to 1:1.

In one embodiment, the formation comprises a porous and permeable rock formation, wherein crude oil and formation brine are contained within a pore space of the rock formation.

In one embodiment, the formation is contacted for a period of time with the preconditioning fluid, after which a aqueous displacement fluid is injected into the formation. During the preconditioning step, the precondition fluid may be injected into the formation and any resulting production fluids, including spent preconditioning fluid, recovered from the formation. Alternatively, sufficient preconditioning fluid may be injected to supply up to 2 pore volumes of fluid to the formation, after which the formation is shut in for a soaking period. During the soaking period, imbibition causes oil trapped in capillaries and pores to migrate to regions of the formation from which production is enhanced. At the conclusion of the soaking period, the aqueous displacement fluid is injected into the formation for displacing hydrocarbons to the production well.

When employed, the soaking period can vary anywhere from an hour to several months, depending on the particular formation. In alternative embodiments, the soaking period ranges in time from 1 day to 20 days; or from 2 days to 7 days.

The aqueous displacement fluid may have the same interfacial tension as the preconditioning fluid. Substantially the same interfacial tension indicates a value between an aqueous phase and a liquid hydrocarbon phase that is within about three times to five times or within one order of magnitude. The liquid hydrocarbon phase may include crude oil recovered from the formation of interest. Comparisons are performed at common pressures and temperatures, such as those characteristic of conditions experienced within the formation of interest. The aqueous displacement fluid is characterized as having an interfacial tension, in contact with the crude oil, that is in a range from 75% to 125% of the interfacial tension of the preconditioning fluid in contact with the crude oil.

The aqueous displacement fluid may have the same viscosity as the preconditioning fluid, or a higher viscosity. Substantially the same viscosity indicates a kinematic viscosity value that is within about a factor of 3, or within a factor of 1.5, at a reservoir temperature and shear rate characteristic of flow through the bulk of the reservoir (e.g., 1 s$^{-1}$).

Such substantially similar viscosities are characteristic of fluids only differing in salinity and generally not those with added polymer viscosifiers. Comparisons are performed at common pressures, temperatures, and shear conditions, preferably those characteristic of conditions experienced within the formation of interest.

The viscosity of the aqueous displacement fluid and/or the preconditioning fluid may be increased by addition of one or more polymer viscosifiers to the fluid. In embodiments, the aqueous displacement fluid contains in a range from 100 to 5000 ppm of polymer.

Polymers, such as those commonly employed for enhanced oil recovery, may be included to control the mobility of the aqueous displacement solution. Such polymers include, but are not limited to, xanthan gum, partially hydrolyzed polyacrylamides (HPAM) and copolymers of 2-acrylamido-2-methylpropane sulfonic acid and/or sodium salt and polyacrylamide (PAM) commonly referred to as AMPS copolymer. Molecular weights (Mw) of the polymers range from about 10,000 daltons to about 20,000,000 daltons, such as about 100,000 to about 500,000, or about 300,000 to 800,000 daltons. Polymers are used in the range of about 250 ppm to about 5,000 ppm, such as about 500 to about 2500 ppm concentration, or about 1000 to 2000 ppm in order to match or exceed the reservoir oil viscosity under the reservoir conditions of temperature and pressure. Examples of polymers include Flopaam™ AN125 and Flopaam™ 3630S, which are produced by and available from SNF Floerger, headquartered in Andrézieux, France.

The aqueous displacement fluid has an ionic strength in a range from 0.001M to 5M. In alternative embodiments, the ionic strength of the aqueous displacement fluid is in a range from 0.001M to 0.03M; or in a range from 0.03M to 0.2M; or in a range from 0.2M to 1M; or in a range from 1M to 5M.

In embodiments, the aqueous displacement fluid does not contain the elastic modifying agent of the preconditioning fluid.

In one embodiment, the invention relates to a computer-implemented method for determining physical and chemical properties of a preconditioning fluid and a displacing fluid. The computer implemented method includes receiving measurement data associated with one or more characteristics of a rock formation sample, a crude oil sample, and a formation brine sample of a subterranean formation. The computer implemented method includes using said measurement data in a predictive model to determine physical and chemical properties of a preconditioning fluid and a displacing fluid for enhancing production of that crude oil from that rock formation. The predictive model sets the physical and chemical properties of the preconditioning fluid such that an interface elasticity of the preconditioning fluid and the crude oil in the rock formation is at least 10% higher than an interface elasticity of the formation brine and the crude oil in the rock formation. The computer implemented method includes outputting the determined physical and the chemical properties of the preconditioning fluid and the displacing fluid. The preconditioning fluid and the displacing fluid with those determined physical and chemical properties can be injected into a wellbore for producing that crude oil from that rock formation.

Figure 2:
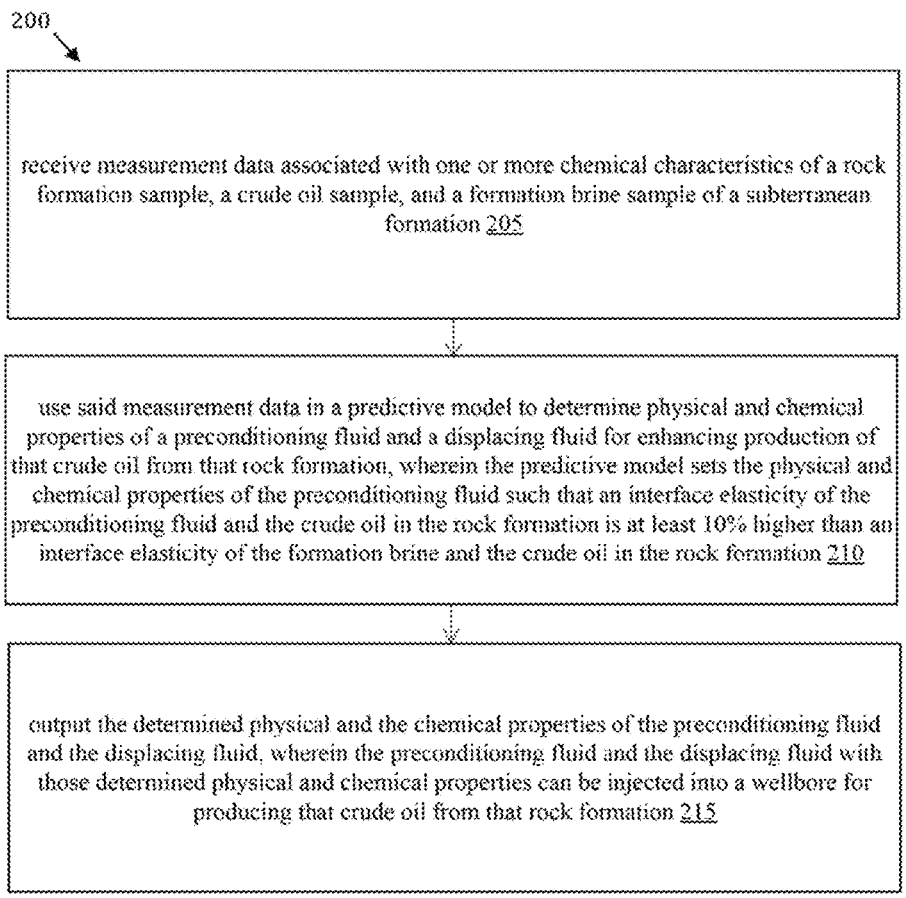
FIG. 2 illustrates one embodiment of a method for determining physical and chemical properties of a preconditioning fluid and a displacing fluid that may be executed using the computing system of FIG. 1.

FIG. 1 illustrates one embodiment of a computing system for determining physical and chemical properties of a preconditioning fluid and a displacing fluid. FIG. 2 illustrates one embodiment of a method for determining physical and chemical properties of a preconditioning fluid and a displacing fluid that may be executed using the computing system of FIG. 1. Turning to FIG. 1, this figure illustrates a computing system 100 useable for determining physical and chemical properties of a preconditioning fluid and a displacing fluid. The computing system 100 can, in example embodiments, be communicatively connected to systems providing data such as measurement data 122 and/or systems for further processing or interpreting the measurement data 122 as described herein. The measurement data 122 can include practically any data such as, but not limited, to the examples provided herein in connection with FIG. 2. In general, the computing system 100 includes at least one processor 105 communicatively connected to at least one memory 104 via at least one data bus 106. The processor 105 can be any of a variety of types of programmable circuits capable of executing computer-readable instructions to perform various tasks, such as mathematical and communication tasks.

The memory 104 can include any of a variety of memory devices, such as using various types of computer-readable or computer storage media. A computer storage medium or computer-readable medium may be any medium that can contain or store the program for use by or in connection with the instruction execution system, apparatus, or device. By way of example, computer storage media may include dynamic random access memory (DRAM) or variants thereof, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally includes at least one or more tangible media or devices. Computer storage media can, in some embodiments, include embodiments including entirely non-transitory components. In the embodiment shown, the memory 104 may store a fluid determination application 112 with a method 200, as discussed in further detail below. However, an application 112 is not necessary.

The computing system 100 can also include a communication interface 108 configured to receive and transmit data, for example, the measurement data 122. For example, the measurement data 122 may be received from a user, received from laboratory equipment, received from other computing systems, etc. Additionally, a display 110 can be used for presenting a graphical display of the fluid determination application 112 or components thereof, for displaying the determined physical and the chemical properties of the preconditioning fluid and the displacing fluid, etc.

Those of ordinary skill in the art will appreciate that although certain terminology is used herein, such as the terms solution, application, component, etc., the invention is not limited to the exact embodiments disclosed herein. For example, embodiments consistent with this disclosure can be performed using computer executable instructions, computer executable code, modules, data structures, graphs, etc., and the embodiments are not limited to any specific arrangement in this disclosure.

Referring generally to the systems and methods herein, and referring to in particular computing systems embodying the methods and systems of the present disclosure, it is noted that various computing systems can be used to perform the processes disclosed herein. For example, embodiments of the disclosure may be practiced in various types of electrical circuits comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, aspects of the methods described herein can be practiced within a general purpose computer or in any other circuits or systems.

Embodiments of the present disclosure can be implemented as a computer process (method), a computing system, or as an article of manufacture, such as a computer program product or computer readable media. Indeed, each method claim herein or method step may have a corresponding apparatus (e.g., computing system) claim and/or computer readable media claim. The term computer readable media as used herein may include computer storage media. Computer storage media may include volatile and nonvolatile, removable and non-removable media implemented in any method or technology for storage of information, such as computer readable instructions, data structures, routines, code, applications, programs, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing system 100, above. Computer storage media does not include a carrier wave or other propagated or modulated data signal. In some embodiments, the computer storage media includes at least some tangible features; in many embodiments, the computer storage media includes entirely non-transitory components.

Embodiments of the present disclosure can be implemented in hardware only, software only, or a combination of hardware and software. Furthermore, embodiments of the present disclosure can include at least one server, at least on client device, a workstation, a distributed setup, a mobile device, etc. depending on the implementation.

Embodiments of the present disclosure, for example, are described herein with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved. Embodiments may include fewer than or more than the functionality/acts provided herein.

Turning to FIG. 2, the computer implemented method 200 may be executed by the computing system 100 of FIG. 1. At 205, the method 200 may receive measurement data associated with one or more chemical characteristics of a rock formation sample, a crude oil sample, and a formation brine sample of a subterranean formation. In one embodiment, the measurement data for the rock formation sample may include Quantitative X-Ray Diffraction (QXRD) analysis data regarding the composition of the rock formation and cation exchange capacity of the rock formation. In one embodiment, the measurement data for the rock formation sample may include thin section analysis data and/or scanning electron microscopy (SEM) analysis data regarding pore geometry, clay morphology, surface area covered by the clay, position of various clays or minerals in the pore space, etc. In one embodiment, the measurement data for the crude oil sample may include SARA (Saturated, Aromatic, Resin, and Asphaltene) analysis data and/or a detailed characterization of the asphaltene. In one embodiment, the measurement data for the formation brine sample may include gas chromatography analysis data.

At 210, the method 200 may use said measurement data in a predictive model to determine physical and chemical properties of a preconditioning fluid and a displacing fluid for enhancing production of that crude oil from that rock formation. The predictive model may set the physical and chemical properties of the preconditioning fluid such that an interface elasticity of the preconditioning fluid and the crude oil in the rock formation is at least 10% higher than an interface elasticity of the formation brine and the crude oil in the rock formation.

In one embodiment, the predictive model may be based on molecular dynamic modelling (e.g., the predictive model may be molecular dynamic modelling, may use molecular dynamic modelling, etc.). Molecular dynamic modelling, sometimes referred to as molecular dynamic simulations (MDS), is explained further in the following documents, and each of these documents is incorporated by reference in its entirety: (a) D. Sergi et al., "Molecular dynamics simulations of the contact angle between water droplets and graphite surfaces," Fluid Phase Equilibria, Vol 332, Oct. 25, 2012, pp 173-177, (b) S. Iglauer et al., "Molecular dynamics computations of brine-CO2 interfacial tensions and brine-CO2-quartz contact angles and their effects on structural and residual trapping mechanisms in carbon geo-sequestration," Journal of Colloid and Interface Science, Vol. 386, 404-414, 2012, and (c) C. M. Tenney et al., "Molecular Simulation of Carbon Dioxide, Brine, and Clay Mineral Interactions and Determination of Contact Angles," Environmental Science & Technology, Vol. 48, 20352042, 2014.

As an example, the molecular dynamic modelling may be used to determine physical and chemical properties of the precondition fluid and the displacing fluid discussed herein. Depending on the embodiment, the molecular dynamic modeling may be used to determine (i) a composition for the preconditioning fluid (e.g., determine a better or more optimal composition for the preconditioning fluid for that crude oil and that formation), (ii) a composition for the displacing fluid (e.g., determine a better or more optimal composition for the displacing fluid for that crude oil and that formation), or (iii) both in response to the received measurement data. The molecular dynamic modelling may also be used to determine other items, such as (iv) temperature of the preconditioning fluid, (v) temperature of the displacing fluid, (vi) injection pressure, (vii) viscosity of the preconditioning fluid, (viii) viscosity of the displacing fluid, etc.

In another embodiment, the predictive model may be based on correlations generated from one or more databases. For example, one correlation may be correlating the composition of the preconditioning fluid to that of the crude oil, formation brine, and rock formation. Another correlation may be correlating the composition of the displacing fluid to that of the crude oil, formation brine, and rock formation. The same or similar items (i)-(viii) discussed above with the predictive model based on molecular dynamic modelling may be determined with a predictive model based on correlations.

Moreover, in one embodiment, the predictive model (e.g., based on molecular dynamic modelling, based on correlations, or other) may be used to determine a more customized or even ideal composition of the preconditioning fluid that may enhance the production of that crude oil in that subterranean formation, such as determine the elasticity modifying agent and quantity, the polymer and quantity, and other additives and their quantities. Similarly, in one embodiment, the predictive model (e.g., based on molecular dynamic modelling, based on correlations, or other) may be used to determine a more customized or even ideal composition of the displacing fluid that may enhance the production of that crude oil in that subterranean formation, such as determine the elasticity modifying agent and quantity, the polymer and quantity, and other additives and their quantities.

Furthermore, in determining the physical and chemical properties of the preconditioning fluid and the displacing fluid, the predictive model may apply constraints. In one embodiment, the predictive model sets the physical and chemical properties of preconditioning fluid such that an interface elasticity of the preconditioning fluid and the crude oil in the rock formation is at least 10% higher than an interface elasticity of the formation brine and the crude oil in the rock formation. In one embodiment, the predictive model sets the physical and chemical properties of the displacing fluid such that an interface elasticity of the displacing fluid and the crude oil in the rock formation is at least 10% higher than an interface elasticity of the formation brine and the crude oil in the rock formation. In one embodiment, the predictive model sets the physical and chemical properties of each fluid such that an Amott-Harvey wettability index of that fluid in contact with that crude oil in that rock formation is in a range from 0.5 to 1 when a flow capacity index (FCI) is in a range from 1 to 3. In another embodiment, the predictive model sets the physical and chemical properties of each fluid such that an Amott-Harvey wettability index of that fluid in contact with that crude oil in that rock formation is in a range from 0.1 to 0.3 when a flow capacity index (FCI) is in a range from less than or equal to 3.

At 215, the method 200 may output the determined physical and the chemical properties of the preconditioning fluid and the displacing fluid. The preconditioning fluid and the displacing fluid with those determined physical and chemical properties can be injected into a wellbore for producing that crude oil from that rock formation. For example, a user receiving or viewing the output via the computing system 200 may then generate the preconditioning fluid and the displacing fluid with those determined physical and chemical properties, and the generated fluids can be injected into a wellbore drilled into that formation to produce that crude oil. For example, the preconditioning fluid may be injected into a wellbore as part of a hydraulic fracturing fluid for hydraulically fracturing the wellbore. Indeed, the induced network of fractures may facilitate more efficient transport of the preconditioning fluid to the treated reservoir volume. Alternatively, the preconditioning fluid may be injected into a wellbore during a flooding operation.

While in the foregoing specification this invention has been described in relation to certain embodiments thereof, and many details have been set forth for purpose of illustration, it will be apparent to those skilled in the art that the invention is susceptible to alteration and that certain other details described herein can vary considerably without departing from the basic principles of the invention.

What is claimed is:

1. A method for enhancing the production of crude oil from a subterranean formation that contains crude oil and formation brine, comprising:
   a. preconditioning the subterranean formation by injecting into an injection well in the subterranean formation a preconditioning fluid for mobilizing crude oil in pore spaces within the subterranean formation, the preconditioning fluid including:
      i. an aqueous base fluid;
      ii. an interface elasticity agent comprising a surface active chemical compound capable of accumulating at an interface between the crude oil and the formation brine to increase an elastic modulus of the interface in an amount such that an interface elasticity between the preconditioning fluid and the crude oil is at least 10% greater than an interface elasticity between the formation brine and the crude oil and such that an interfacial tension between the preconditioning fluid and the crude oil is within a factor of 3 of an interfacial tension between the formation brine and the crude oil: and
      iii. a salt in an amount to impart an ionic strength to the preconditioning fluid such that the subterranean formation in contact with the preconditioning fluid has a desired Amott-Harvey, wettability index for the subterranean formation;
   b. allowing the preconditioning fluid to be imbibed into the pore spaces within the subterranean formation such that the interface elasticity agent is adsorbed on the interface between the preconditioning fluid and the crude oil, to increase an elasticity a the interface between the preconditioning fluid and the crude oil:
   c. displacing the preconditioning fluid from the subterranean formation using an aqueous displacement fluid haying an ionic strength within a factor of 1.5 of the ionic strength of the preconditioning fluid for displacing the crude oil in the subterranean formation to a production well; and
   d. recovering crude oil from the subterranean formation through the production well:
   wherein the injecting of the preconditioning fluid results in enhanced mobilization of crude oil in the pore spaces within the subterranean formation, increased oil recovery and decreased crude oil that is left behind in the subterranean formation.

2. The method of claim 1, wherein the aqueous displacement fluid contains in a range from 100 to 5000 mg/l of a polymer.

3. The method of claim 1, wherein the preconditioning fluid contains in a range from 100 to 5000 mg/l of a polymer.

4. The method of claim 1, wherein the subterranean formation in contact with the preconditioning fluid has an Amott-Harvey wettability index in a range from 0.1 to 0.3 and a flow capacity index (FCI) in a range from 1 to 3.

5. The method of claim 1, wherein the subterranean formation in contact with the preconditioning fluid has an Amott-Harvey wettability index in a range from (0.5 to 1.0 and a flow capacity index (FCI) greater than 3.

6. The method of claim 5, wherein the preconditioning fluid has an ionic strength in a range from 0.01M to 0.4M.

7. The method of claim 1, wherein sufficient preconditioning fluid is injected into the subterranean formation, such that a region of the subterranean formation that encompasses at least one injection wellbore and at least one production wellbore in the subterranean formation has an Amott-Harvey wettability index in a range from 0 to 1.0.

8. The method of claim 1, wherein the preconditioning fluid has an ionic strength in a range from 0.001M to 5M.

9. The method of claim 1, wherein the base fluid comprises production fluid from the subterranean formation.

10. The method of claim 1, wherein the interface elasticity between the preconditioning fluid and the crude oil is in a range from 0.0001 to 10 Pa m.

11. The method of claim 1, wherein the preconditioning fluid comprises an interface elasticity agent selected from the group consisting of alkylaryl alkoxy alcohols, alkyl alkoxy alcohols, alkyl alkoxylated esters, and alkyl polyglycosides.

12. The method of claim 1, wherein the preconditioning fluid comprises an interface elasticity agent based on a silicone copolymer, a resin, a non-ionic surfactant, and combinations thereof.

13. The method of claim 1, wherein the preconditioning fluid comprises the interface elasticity agent in a range from 0.01 to 1000 ppm.

14. The method of claim 1, wherein the interfacial tension between the crude oil and the preconditioning fluid is in a range from 10 to 45 mN/m.

15. The method of claim 1, further comprising:
soaking at least a portion of the subterranean formation with from 0.1 to 0.75 pore volumes of the preconditioning fluid for a period of time of from 1 day to 300 days prior to displacing the preconditioning fluid from the subterranean formation using the aqueous displacement fluid.

16. The method of claim 1 wherein the interface elasticity agent comprises a compound selected from the group consisting of an alcohol, an alkylaryl alkoxy alcohol, an alkyl alkoxy alcohol, an alkyl alkoxylated ester, an alkyl polyglycoside, a surfactant, a nonionic surfactant, an anionic surfactant, a resin, a nonionic alcohol, a nonionic ester, a silicone copolymer and combinations thereof.

17. The method of claim 1, wherein the interface elasticity agent is a silicone copolymer based on polyalkylene oxide modified poly (dimethylsiloxane) chains.

18. The method of claim 1, wherein the subterranean formation in contact with the preconditioning fluid has an Amott-Harvey wettability index in a range from 0 to 1.0.

19. A method for enhancing the production of crude oil from a subterranean formation that contains crude oil and formation brine, comprising:
collecting a production brine sample, a crude oil sample and a formation matrix sample from the subterranean formation;
determining an interfacial tension of the production brine sample in contact with the crude oil sample and an interface elasticity of an interface between the crude oil sample and the production brine sample;
determining an Amott-Harvey wettability index of the formation matrix sample in contact with the crude oil sample and the production brine sample;
forming a preconditioning fluid for use in the subterranean formation, the preconditioning fluid comprising:
an aqueous base fluid comprising from 500 to 200,000 mg/l TDS;
a salt in an amount wherein the preconditioning fluid has an ionic strength such that the formation matrix sample in contact with the preconditioning fluid and the crude oil sample has an Amott-Harvey wettability index in a range from 0 to 1; and
an interface elasticity agent in an amount wherein an interface elasticity between the preconditioning fluid and the crude oil is at least 10% greater than the interface elasticity between the crude oil sample and the production brine sample; and an interfacial tension between the preconditioning fluid and the crude oil sample is within a factor of 3 of the interfacial tension between the production brine sample and the crude oil sample.

* * * * *